United States Patent
Schroeder et al.

(10) Patent No.: US 10,980,726 B2
(45) Date of Patent: Apr. 20, 2021

(54) HAIR CARE SHAMPOO

(71) Applicant: Henkel AG & Co. KGaA, Dusseldorf (DE)

(72) Inventors: Thomas Schroeder, Hamburg (DE); Soeren Scheele, Pinneberg (DE); Manuela Mette, Kleinfeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 55 days.

(21) Appl. No.: 16/281,975

(22) Filed: Feb. 21, 2019

(65) Prior Publication Data

US 2019/0282479 A1   Sep. 19, 2019

(30) Foreign Application Priority Data

Feb. 23, 2018 (DE) .................. 10 2018 202 804

(51) Int. Cl.
  *A61K 8/42* (2006.01)
  *A61K 8/92* (2006.01)
  *A61K 8/73* (2006.01)
  *A61Q 5/02* (2006.01)
  *A61K 8/37* (2006.01)

(52) U.S. Cl.
  CPC ............... *A61K 8/375* (2013.01); *A61K 8/42* (2013.01); *A61K 8/737* (2013.01); *A61K 8/922* (2013.01); *A61K 2800/262* (2013.01); *A61K 2800/34* (2013.01); *A61K 2800/5426* (2013.01); *A61K 2800/596* (2013.01); *A61Q 5/02* (2013.01)

(58) Field of Classification Search
  None
  See application file for complete search history.

(56) References Cited

U.S. PATENT DOCUMENTS 9,066,859 B1 * 6/2015 Rizk ....................... A61K 8/042
2017/0189325 A1 * 7/2017 Wilson ................... A61Q 19/00

FOREIGN PATENT DOCUMENTS

CN          103284911 A1       9/2013

* cited by examiner

Primary Examiner — Melissa S Mercier
(74) Attorney, Agent, or Firm — Lorenz & Kopf, LLP

(57) ABSTRACT

Hair cleaning agents and methods for improving the care properties of hair are provided. An exemplary hair cleaning agent contains anionic surfactant and a specific oil mixture. The oil mixture may include (i) at least one mono- and/or diester of glycerol and a saturated or unsaturated, branched or unbranched carboxylic acid having 18 to 30 carbon atoms, (ii) at least one vegetable oil, (iii) at least one cationic guar polymer, and (iv) at least one amidoamine of a selected formula.

15 Claims, No Drawings

HAIR CARE SHAMPOO

CROSS-REFERENCE TO RELATED APPLICATION

This application claims priority to German Patent Application No. 10 2018 202 804.4, filed Feb. 23, 2018, which is incorporated herein by reference in its entirety.

TECHNICAL FIELD

The application describes cosmetic cleaning agents based on anionic surfactants and a care-active substance combination comprising a specific oil mixture, cationic guar polymers and amidoamines.

The application further describes the use of these agents for improving the care properties of hair.

BACKGROUND

Human hair and the scalp can be cleansed and freed of sebum, styling residue and other contaminants with the help of cosmetic cleaning agents (hair shampoos).

Due to the (mostly anionic) surfactants usually contained in cosmetic hair cleaning agents, hair cleaning is always associated with the removal of lipids and proteins from the hair or scalp, in which damage to the hair structure and/or dehydration of the scalp can occur, in particular with frequent cleaning.

Damage to the hair structure or the hair fibers, in particular split ends and/or hair breakage, can also be promoted by environmental influences (such as intense sunlight), mechanical stress (such as combing under hair dryer) and by chemical influences (such as dyeing, deforming or straightening the hair).

In order to prevent and/or reduce hair damage, different care substances such as cationic care polymers, mineral or vegetable oils and/or silicones have been added to hair shampoos in the past. This already resulted in significantly improved care properties such as combability and hair feel from the first application.

However, disadvantages also appear with regular use over a long period of time. Thus, the regular deposition of higher amounts of oil from care shampoos on the hair ensures the aforementioned conditioning benefits, but at the same time—in particular after regular application to fine and/or damaged hair—a certain over-conditioning can be observed, whereby the hair looks greasy and weighted. Overall, the hair thus has an unkempt, unattractive appearance.

A further disadvantage is that higher amounts of oil in shampoos must be stabilized with effort by the incorporation of excipients, such as special thickening polymers and/or alkoxylated nonionic emulsifiers and usually lead to milky-turbid formulations.

Due to the increasing number of incompatibilities, the consumer desires less complex cosmetic agents which have a high proportion of active substances and excipients of natural origin which are readily degradable.

For the consumer, this is synonymous with transparent formulations.

The partial or total abandonment of oils in shampoos in favor of other care substances such as cationic care substances leads to unwanted flying of the hair and does not provide a solution to the aforementioned problem.

The present application was therefore based on the object of providing a hair care agent having high care performance, which ensures an optimal balance between mild and thorough cleaning, long-lasting and sustainable care and good compatibility. In order to avoid the over-conditioning effects described, ideally the use of larger amounts of oil, in particular the use of silicones or mineral oils, should be therefore dispensed with.

Another goal was to provide transparent hair care shampoos.

BRIEF SUMMARY

An exemplary hair cleaning agent is provided and includes at least one anionic surfactant and a mixture of oils. In an exemplary embodiment, the mixture of oils includes (i) at least one mono- and/or diester of glycerol and a saturated or unsaturated, branched or unbranched carboxylic acid having 18 to 30 carbon atoms, (ii) at least one vegetable oil, (iii) at least one cationic guar polymer, and (iv) at least one amidoamine of the formula (I)

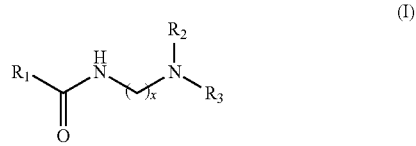

wherein $R_1$ stands for a saturated or unsaturated, branched or unbranched alk(en)yl radical having 19 to 30 carbon atoms, $R_2$ and $R_3$ independently stand for hydrogen or a $C_1$-$C_4$ alkyl group, and x stands for an integer from 2 to 6.

A method for improving the care properties of hair is also provided and includes applying a hair cleaning agent to the hair, the hair cleaning agent including at least one anionic surfactant and a mixture of oils. In an exemplary embodiment, the mixture of oils includes (i) at least one mono- and/or diester of glycerol and a saturated or unsaturated, branched or unbranched carboxylic acid having 18 to 30 carbon atoms, (ii) at least one vegetable oil, (iii) at least one cationic guar polymer, and (iv) at least one amidoamine of the formula (I)

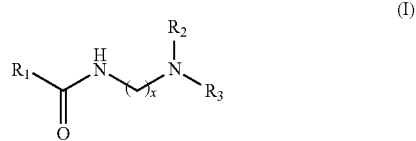

wherein $R_1$ stands for a saturated or unsaturated, branched or unbranched alk(en)yl radical having 19 to 30 carbon atoms, $R_2$ and $R_3$ independently stand for hydrogen or a $C_1$-$C_4$ alkyl group, and x stands for an integer from 2 to 6.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has been found that hair care shampoos having excellent cleaning and care effects can be provided by combining anionic surfactants with a care active substance mixture of cationic guar polymers, specific amidoamines and small amounts of a specific oil mixture. The hair care shampoos are very well tolerated by the skin and, even with regular use, do not lead to a so-called built-up effect.

The use of polymeric or alkoxylated nonionic stabilizing agents can be dispensed with for the production and storage of the shampoos, so that compositions of high transparency can be provided.

In particular, the gloss, volume, feel and softness of hair could be improved by the use of the agents.

A first subject of this application is thus a hair cleaning agent, which contains
a) at least one anionic surfactant,
b) a mixture of oils containing
i. at least one mono- and/or diester of glycerol and a saturated or unsaturated, branched or unbranched carboxylic acid having from about 18 to about 30 carbon atoms, and
ii. at least one vegetable oil,
c) at least one cationic guar polymer and
d) at least one amidoamine of the formula (I),

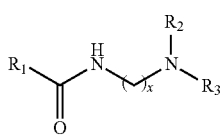

(I)

wherein
$R_1$ stands for a saturated or unsaturated, branched or unbranched alk(en)yl radical having from about 19 to about 30 carbon atoms,
$R_2$ and $R_3$ independently stand for hydrogen or a $C_1$-$C_4$ alkyl group, and
x stands for an integer from 2 to 6.

Particularly preferred hair cleaning agents according to a first preferred embodiment (based on the total weight of the agent) contain
from about 4.00 to about 25.00% by weight of at least one anionic surfactant a),
from about 0.10 to about 5.00% by weight of at least one mono- and/or diester b)
from about 0.01 to about 1.00% by weight of at least one vegetable oil b)
from about 0.01 to about 1.00% by weight of at least one cationic guar polymer c),
from about 0.01 to about 2.00% by weight of at least one amidoamine d) according to formula (I).

The hair cleaning agents as contemplated herein preferably contain the active substances a) to d) in a cosmetically acceptable carrier. For the purposes of the present disclosure, this is preferably understood to mean an aqueous or aqueous-alcoholic carrier.

The cosmetic carrier preferably contains at least about 75% by weight, more preferably at least about 77% by weight, particularly preferably at least about 78% by weight and in particular preferably at least about 80% by weight of water.

Furthermore, the cosmetic carrier can contain from about 0.50 to about 10% by weight, preferably from about 0.75 to about 9% by weight and in particular from about 1.00 to about 6% by weight of at least one alcohol.

Suitable alcohols are, for example, ethanol, ethyl diglycol, 1-propanol, 2-propanol, isopropanol, 1,2-propylene glycol, glycerol, diglycerol, triglycerol, 1-butanol, 2-butanol, 1,2-butanediol, 1,3-butanediol, 1-pentanol, 2-pentanol, 1,2-pentanediol, 1,5-pentanediol, 1-hexanol, 2-hexanol, 1,2-hexanediol, 1,6-hexanediol, polyethylene glycols, sorbitol, sorbitan, benzyl alcohol, phenoxyethanol or mixtures of these alcohols.

Particularly preferred are polyols, because it has been found that they can further support the care effect of the active substance complex as contemplated herein without negatively influencing the foam properties of the agents. In addition, a certain polyol content contributes to the better solubilization of the specific oil mixture in the hair cleaning agents, which it is whereby possible to dispense entirely with polymeric stabilizers and/or alkoxylated nonionic emulsifiers.

A particularly preferred polyol is glycerol, which can be used in the agents as contemplated herein in the aforementioned amounts.

A first essential component of the care active substance mixture in the hair cleaning agents as contemplated herein is a mono- and/or diester b), i., which is selected from mono- and/or diesters of glycerol and unsaturated carboxylic acids having from about 18 to about 24 carbon atoms.

Preference is given to mono- and/or diesters b) i., which can be dissolved and/or solubilized very well and without polymeric and/or alkoxylated nonionic excipients in the hair cleaning agents as contemplated herein, so that clear formulations can be obtained.

Especially suitable are mono- and/or diesters of glycerol and petroselinic acid, oleic acid, gadoleic acid, gondoic acid, cetoleic acid, erucic acid, linoleic acid and/or linolenic acid, since they are also accessible from natural (plant) sources and are readily biodegradable.

Particularly preferred is a mono- and/or diester of glycerol and oleic acid (International Nomenclature Cosmetic Ingredient (INCI) name: Glyceryl Oleate), because these esters have excellent lipid replenishing properties and improve the combability and feel of the hair.

The one or more monoesters and/or diesters of glycerol and unsaturated carboxylic acids having from about 18 to about 24 carbon atoms b) i. is (are) used in the hair cleaning agents as contemplated herein, based on the total weight of the agent, preferably in an amount of from about 0.10 to about 5.00% by weight, more preferably from about 0.20 to about 4.00% by weight, particularly preferably from about 0.30 to about 3.00% by weight, very particularly preferably from about 0.40 to about 2.00% by weight and in particular from about 0.50 to about 1.00% by weight.

In a preferred embodiment, a mono- and/or diester of glycerol and oleic acid (INCI name: Glyceryl Oleate) is used in the aforementioned amounts in the hair cleaning agent as contemplated herein.

A second essential component of the care active substance mixture in the hair cleaning agents as contemplated herein is a vegetable oil.

Suitable oils are, for example, amaranth seed oil, apricot kernel oil, argan oil, avocado oil, babassu oil, cottonseed oil, borage seed oil, camelina oil, canola oil, cranberry oil, thistle oil, peanut oil, pomegranate kernel oil, grapefruit seed oil, hemp oil, rose hip kernel oil, hazelnut oil, elderflower seed oil, currant seed oil, jojoba oil, cocoa butter, coconut oil, pumpkin seed oil, linseed oil, macadamia nut oil, maize germ oil, mallow oil, almond oil, mango seed oil, marula oil, poppy seed oil, evening primrose oil, olive oil, palm oil, palm kernel oil, peach kernel oil, rambutan oil, rapeseed oil, rice bran oil, castor oil, sacha inchi oil, safflower oil, sea buckthorn pulp oil, sea buckthorn seed oil, sasanqua oil, sesame oil, shea butter, soybean oil, sunflower oil, tea tree oil, grapeseed oil, tsubaki oil, walnut oil, wheat germ oil, meadowfoam seed oil and/or wild rose oil.

Preferred are amaranth seed oil, apricot kernel oil, argan oil, avocado oil, coconut oil, almond oil, macadamia nut oil, rosehip seed oil, sunflower oil, olive oil, peach kernel oil, and/or jojoba oil.

It was found that vegetable oils, also used in low concentrations, in combination with the esters b) i. ensure the aforementioned conditioning benefits on the hair without occurrence of a built-up effect when used regularly. In addition, it could be observed that a combination of the two oils b) i. and ii. in the care active substance mixture of the hair cleaning agents as contemplated herein could significantly improve the anti-static properties and the gloss of the treated hair.

The vegetable oil(s) b) ii. is (are) used in the hair cleaning agents as contemplated herein, based on the total weight of the agent, preferably in an amount of from about 0.01 to about 1.00% by weight, more preferably from about 0.02 to about 0.80% by weight, particularly preferably from about 0.03 to about 0.60% by weight, most preferably from about 0.04 to about 0.40% by weight and in particular from about 0.05 to about 0.20% by weight.

A third essential component of the care active substance mixture in the hair cleaning agents as contemplated herein is a cationic guar polymer c). Suitable cationic guar polymers are available from natural sources and give the hair a soft feel. They furthermore support the separation of the oils on the hair without negatively influencing the hair volume in the care active substance mixture of the hair cleaning agents as contemplated herein.

In the context of the present disclosure, suitable cationic guar polymers c) are understood to mean physiologically compatible cationic guar derivatives and/or hydrophobically modified cationic guar derivatives.

Preference is given to cationic hydroxy ($C_1$-$C_4$) alkyl guar derivatives, preferably cationic hydroxyethyltrimethylammonium guar and/or cationic hydroxypropyltrimethylammonium guar having average molecular weights (weight average) from about 100,000 to about 2,000,000 daltons, preferably from about 200,000 to about 1,750,000 daltons and in particular from about 300,000 to about 1,600,000 daltons. Further preferred are cationic hydroxy ($C_1$-$C_4$) alkyl guar derivatives, preferably cationic hydroxyethyltrimethylammonium guar and/or cationic hydroxypropyltrimethylammonium guar, having cationic charge densities of at least about 0.5 meq/g.

Especially preferred are the cationic guar polymers known under the INCI name Guar Hydroxypropyltrimonium Chloride having a molecular weight (weight average) from about 100,000 to about 2,000,000 daltons, preferably from about 200,000 to about 1,750,000 daltons and in particular from about 300,000 to about 1,600,000 daltons and a cationic charge density of at least about 0.5 meq/g.

Suitable cationic guar polymers c) are available, for example, under the trade names "Jaguar®" oder "N-Hance®" from different suppliers.

Particularly suitable cationic guar polymers c) are: Jaguar® C13S, Jaguar® C 162, Jaguar® C14S, Jaguar® C17, Jaguar® Excel, N-Hance® 3196 and/or N-Hance® 3215.

The hair cleaning agents as contemplated herein contain the cationic guar polymer(s) c) preferably in an amount of from about 0.01 to about 1.00% by weight, more preferably from about 0.02 to about 0.90% by weight, particularly preferably from about 0.03 to about 0.75% by weight, most preferably from about 0.04 to about 0.60% by weight and in particular from about 0.05 to about 0.50% by weight, wherein the quantities refer to the total weight of the hair cleaning agent.

A fourth essential component of the care active substance mixture in the hair cleaning agents as contemplated herein is an amidoamine of the formula (I),

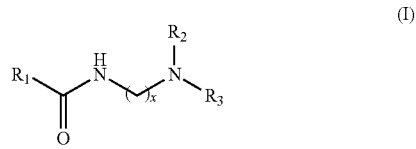

wherein
$R_1$ stands for a saturated or unsaturated, branched or unbranched alk(en)yl radical having from about 19 to about 30 carbon atoms,
$R_2$ and $R_3$ independently stand for hydrogen or a $C_1$-$C_4$ alkyl group, and x stands for an integer from 2 to 6.

Amidoamines d) of formula (I) give hair a very soft, supple feel without weighing it down. It has been found that, in particular, amidoamines d) having an alk(en)yl radical ($R_1$) comprising more than about 19 carbon atoms also improve combability and are better suitable than the amidoamines (alk(en)yl radical having <18 C atoms) customarily used in the prior art in preventing a built-up effect.

Particularly suitable are therefore amidoamines d) according to formula (I), wherein
$R_1$ stands for an alkenyl radical having from about 20 to about 24 carbon atoms,
$R_2$ and $R_3$ stands for methyl groups, and
x stands for the numbers 2, 3 or 4.

Particularly preferred for use in the hair cleaning agents as contemplated herein are amidoamines d) according to formula (I) which are selected from amidoamines known under the INCI name Brassicamidopropyl Dimethylamine.

Such amidoamines are commercially available from different suppliers and are particularly suitable for use in the agents as contemplated herein; for example, Kerabase® LC from Inolex Personal Care Ingredients, ProCondition® 22 from Inolex Personal Care Ingredients and/or Amidet® APA-22 from Kao Corporation.

The amidoamine(s) is (are) used in the hair cleaning agents as contemplated herein, based on the total weight of the agent, preferably in an amount of from about 0.01 to about 2.00% by weight, more preferably from about 0.05 to about 1.75% by weight, particularly preferably from about 0.10 to about 1.50% by weight, most preferably from about 0.20 to about 1.25% by weight and in particular from about 0.25 to about 1.00% by weight.

For a very good (head) skin compatibility, it is advantageous when the hair cleaning agent as contemplated herein has a slightly acidic pH.

It has been found that hair cleaning agents as contemplated herein in a pH range from about 4.0 to about 6.0 have particularly good skin tolerance and mildness.

In a further preferred embodiment, the hair cleaning agents as contemplated herein therefore have a pH in the range from about 4.0 to about 6.0, more preferably from about 4.2 to about 5.9 and in particular preferably from about 4.5 to about 5.8.

The mildness and foam properties of the hair cleaning agents according to the present disclosure can be particularly controlled by the careful selection of surfactant amounts and/or types of surfactants.

The hair cleaning agents as contemplated herein contain at least one anionic surfactant a) which is essential for the production of satisfactory amounts and properties of foam. To achieve an optimum balance between mildness and foam properties of the hair cleaning agents as contemplated herein, a mixture of at least one anionic surfactant a) with at least one mild co-surfactant has been found, which can preferably be selected from amphoteric and/or zwitterionic and/or nonionic surfactants.

The hair cleaning agents as contemplated herein particularly preferably contain, in addition to the at least one anionic surfactant a), based on the total weight of the agent,
from about 0.10 to about 5.00% by weight of at least one amphoteric and/or zwitterionic surfactant and/or
from about 0.05 to about 3.00% by weight of at least one nonionic surfactant.

Suitable anionic surfactant types a) which can be used in the hair cleaning agents as contemplated herein include, for example:
linear and branched fatty acids having from about 8 to about 30 carbon atoms (soaps),
ether carboxylic acids of the formula R—O—(CH$_2$—CH$_2$O)$_x$—CH$_2$—COOH, in which R is a linear or branched, saturated or unsaturated alkyl group having from about 8 to about 30 C atoms and x=0 or 1 to 16,
acylsarcosides having from about 8 to about 24 C atoms in the acyl group (sarcosinate surfactants),
acyltaurides having from about 8 to about 24 C atoms in the acyl group (taurate surfactants),
acyl isethionates having from about 8 to about 24 C atoms in the acyl group (isethionate surfactants),
sulfosuccinic acid mono- and/or dialkyl esters having from about 8 to about 24 C atoms in the alkyl group and sulfosuccinic acid monoalkylpolyoxyethyl esters having from about 8 to about 24 C atoms in the alkyl group and from about 1 to about 6 oxyethyl groups (sulfosuccinate surfactants),
alpha-olefinsulfonates having from about 8 to about 24 C atoms (alpha-olefin sulfonate surfactants),
alkyl sulfates and/or alkyl ether sulfate salts of the formula R—(OCH$_2$—CH$_2$)$_n$—O—SO$_3$X, in which R preferably means a straight-chain or branched, saturated or unsaturated alkyl group having from about 8 to about 30 C atoms, x the number 0 or from about 1 to about 12 and X an alkali, alkaline earth, ammonium or alkanolamine ion,
sulfonates of unsaturated fatty acids having from about 8 to about 24 C atoms and from about 1 to about 6 double bonds,
Esters of tartaric acid and citric acid with alcohols which represent addition products of about 2 to about 15 molecules of ethylene oxide and/or propylene oxide with fatty alcohols having from about 8 to about 22 C atoms, and/or
alkyl and/or alkenyl ether phosphates of the formula

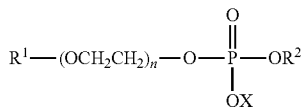

in which R$_1$ preferably stands for an aliphatic hydrocarbon radical having from about 8 to about 30 carbon atoms, R$^2$ for hydrogen, a radical (CH$_2$CH$_2$O)$_n$R$^1$ or X, n for numbers 0 to about 10 and X for hydrogen, an alkali metal or alkaline earth metal or the group —NR$^3$R$^4$R$^5$R$^6$, with R$^3$ to R$^6$ independently of one another standing for a C$_1$ to C$_4$ hydrocarbon radical.

Particular preference is given to alkyl sulfates and/or alkyl ether sulfate salts, ether carboxylic acids, isethionates, taurates and/or alpha-olefin sulfonates, in particular alkyl sulfates and/or alkyl ether sulfate salts.

The anionic surfactant is (are) used in the hair cleaning agents as contemplated herein, based on the total weight of the agent, preferably in an amount of from about 4.00 to about 25.00% by weight, more preferably from about 5.00 to about 20.00% by weight, particularly preferably from about 5.50 to about 17.50% by weight, most preferably from about 6.00 to about 15.00% by weight and in particular from about 6.50 to about 12.50% by weight.

In a preferred embodiment, as anionic surfactant a), at least one alkyl sulfate and/or alkyl ether sulfate salt, ether carboxylic acid, isethionate, taurate and/or alpha-olefinsulfonate, in particular an alkyl sulfate and/or alkyl ether sulfate salt, is used in the aforementioned amounts in the hair cleaning agent as contemplated herein.

Suitable amphoteric and/or zwitterionic surfactant types which can be used in the hair cleaning agents as contemplated herein include, for example, one or more compounds of the following formulas (i) to (vii). In this formula, the radical R preferably stands for a straight-chain or branched, saturated or mono- or polyunsaturated alkyl or alkenyl radical having from about 7 to about 23 carbon atoms (formulas (i) and (ii)) or for a straight-chain or branched, saturated or mono- or polyunsaturated alkyl or alkenyl radical having from about 8 to about 24 carbon atoms (formulas (iii) to (vii)):

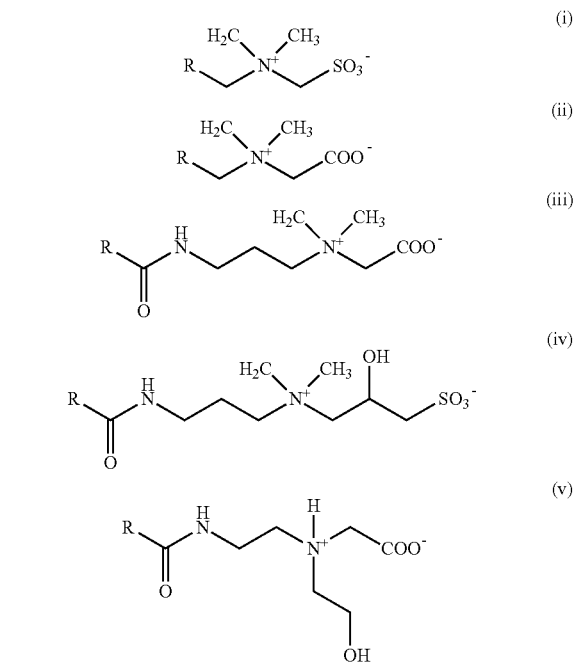

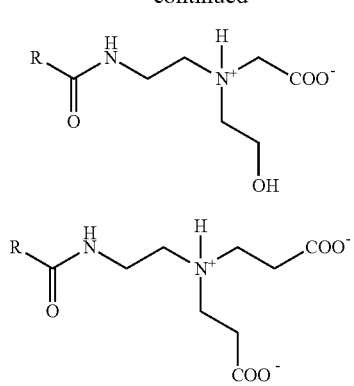
(vi)

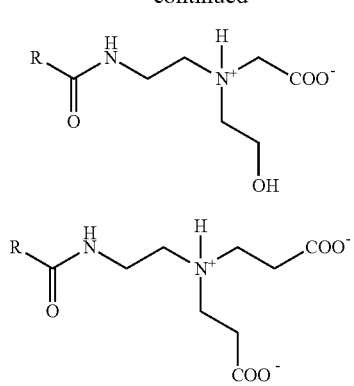
(vii)

Preferred amphoteric surfactants of the aforementioned formulas (i) to (vii) contain, as radical R, predominantly a straight-chain or branched, saturated, mono- or polyunsaturated alkyl radical having from about 8 to about 20, more preferably from about 8 to about 18 and in particular from about 8 to about 16 C atoms.

Particularly preferred are amphoteric surfactants b), in which the radical R is derived from coconut oil.

Most preferred are the amphoteric surfactants known under the INCI names Sodium Cocoamphoacetate, Disodium Cocoamphodiacetate, Sodium Lauroamphoacetate, Sodium Lauroamphodiacetate, Sodium Cocoamphopropionate, Disodium Cocoamphodipropionate, Coco Betaine, Lauryl Betaine Cocamidopropylbetain and/or Lauramidopropylbetain and commercially available from multiple providers.

Especially preferred are surfactants having the INCI names Cocamidopropylbetain, Lauramidopropylbetain, Cocoampho(di)acetate and/or Lauroapho(di)acetate.

The amphoteric and/or zwitterionic co-surfactant(s) in the hair cleaning agents according to the present disclosure (based on their total weight) is (are) preferably used in an amount of from about 0.10 to about 5.00% by weight, more preferably from about 0.50 to about 5.00% by weight, particularly preferably from about 1.00 to about 5.00% by weight and in particular from about 2.00 to about 5.00% by weight.

Particularly preferred anionic surfactants a) in the context of the present disclosure are alkyl (ether) sulfates based on their excellent foam properties. These are, to increase the mildness, preferably combined with cocamidopropyl betaine and/or cocoampho(di)acetate as a co-surfactant.

For some applications, for example, for the cleaning and care of heavily damaged hair and/or very fine hair and/or baby or toddler hair, it can be advantageous to dispense with the use of sulfate surfactants.

However, dispensing with sulfate surfactants often involves a dramatic deterioration in foam properties (quantity and quality), making the selection of suitable surfactants very tedious. The incorporation of oil-based care substances in hair cleaning agents also has a negative impact on the stability, viscosity and foam properties of the agents.

It has been found that nourishing hair cleaning agents having good foam properties and excellent care potential can be produced when at least one surfactant selected from the group of anionic taurate surfactants and/or isethionate surfactants and/or alpha-olefin sulfonate surfactants is selected as an anionic, sulfate-free surfactant base a). Preferably, at least one of these surfactants is combined with cocamidopropyl betaine and/or cocoampho(di)acetate as a cosurfactant.

Suitable nonionic surfactants for use as a co-surfactant are, for example—amine oxides, which can be selected from compounds of the general formulas (I) or (II)

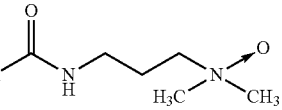
(I)

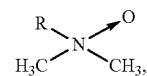
(II)

in which R in each case represents a straight-chain or branched, saturated or mono- or polyunsaturated alkyl or alkenyl radical having from about 6 to about 24 carbon atoms, preferably having from about 8 to about 18 carbon atoms.

Particularly preferred are the surfactants of the aforementioned formula (I) or (II) known under the INCI names Cocamine Oxide, Lauramine Oxide and/or Cocamidopropylaminoxide and commercially available from different suppliers.

Fatty acid alkanolamides of the following general formula,

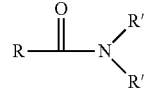

in which R preferably means a linear or branched, saturated or unsaturated alkyl or alkenyl radical having from about 8 to about 24 carbon atoms and the radicals R' stand for hydrogen or for the group —$(CH_2)_n$OH in which n means the numbers 2 or 3 with the proviso that at least one of the radicals R' stands for the aforementioned radical —$(CH_2)_n$OH, mixtures of alkyl (oligo) glucosides and fatty alcohols, for example, the commercially available product Montanov®68, Sterols. Sterols are understood to mean a group of steroids which carry a hydroxyl group at C-atom 3 of the steroid skeleton and are isolated both from animal tissue (zoosterols) and from vegetable fats (phytosterols). Examples of zoosterols are cholesterol and lanosterol. Examples of suitable phytosterols are ergosterol, stigmasterol and sitosterol. Mushrooms and yeasts are also used to isolate sterols, the so-called mycosterols.

Phospholipids. These include, primarily, the glucose phospholipids which are obtained, for example, as lecithins or phosphatidylcholines from, for example, egg yolks or plant seeds (for example, soybeans), Alkyl (oligo)glycosides. Suitable alkyl (oligo)glycosides can be selected from compounds of the general formula RO—$[G]_x$, in which [G] is preferably derived from aldoses and/or ketoses having from about 5 to about 6 carbon atoms, preferably glucose.

The index number x stands for the degree of oligomerization (DP), that is, for the distribution of the mono- and oligoglycosides. The index number x preferably has a value in the range from about 1 to about 10, particularly preferably in the range from about 1 to about 3, which need not be an integer, but rather a fractional number, which can be determined analytically.

Particularly preferred alkyl (oligo)glycosides have a degree of oligomerization between from about 1.2 and about 1.5.

The radical R preferably stands for at least one alkyl and/or alkenyl radical having from about 4 to about 24 C atoms.

Particularly preferred alkyl (oligo)glycosides are the compounds known under the INCI names Caprylyl/Capryl Glucoside, Decyl Glucoside, Lauryl Glucoside and Coco Glucoside.

Particularly preferred nonionic surfactants which can be present as a co-surfactant in the compositions as contemplated herein are fatty acid alkanolamides, alkyl (oligo) glucosides and amine oxides. Particularly preferred are alkyl (oligo)glucosides which, for example, can be used in the agents as contemplated herein as a mixture with the ester b) i. Corresponding products are commercially available, for example under the name Lamesoft® PO 65 from BASF.

The nonionic co-surfactant(s) is (are) used in the hair cleaning agents as contemplated herein (based on their total weight) preferably in an amount of from about 0.05 to about 3.00% by weight, more preferably from about 0.10 to about 2.50% by weight, particularly preferably from about 0.20 to about 2.25% by weight and in particular from about 0.30 to about 2.00% by weight.

Particular preferably in the hair cleaning agents as contemplated herein, an alkyl (oligo)glucoside is used in the aforementioned amounts.

In a further preferred embodiment, the hair cleaning agents as contemplated herein for adjusting the pH, but at the same time also for supporting the hair care properties, additionally contain at least one hydroxycarboxylic acid in a preferred amount (based on the total weight of the agent) from about 0.10 to about 5.00% by weight, more preferably from about 0.20 to about 4.00% by weight, particularly preferably from about 0.30 to about 3.00% by weight and in particular from about 0.40 to about 2.00% by weight.

Suitable hydroxycarboxylic acids are preferably understood to mean alpha-hydroxycarboxylic acids and, in particular, for example, in fruit acids, naturally occurring alpha-hydroxycarboxylic acids.

These include, for example, malic acid, citric acid, glycolic acid, isocitric acid, mandelic acid, lactic acid, tartronic acid and/or tartaric acid.

Suitable hydroxycarboxylic acids furthermore are understood to mean the dicarboxylic acids glutamic acid and/or succinic acid.

Particularly preferred are citric acid, lactic acid, glutamic acid and/or succinic acid.

Particularly good stability and particularly good hair care results (in particular with regard to hair shine and sensory properties such as softness and smoothness) without occurrence of over-conditioning (oily, weighted hair) can be achieved when the hair cleaning agents as contemplated herein in addition to the aforementioned active substances, contain
  no further fat phase components, in particular no silicone oils and/or mineral oils and/or b) i. different fatty acid esters, and
  no nonionic, alkoxylated emulsifiers and/or c) different polymeric thickening agent.

In a further preferred embodiment, hair cleaning agents as contemplated herein are therefore essentially free of silicones and/or mineral oils and/or of b) i. different fatty acid esters.

"Substantially free" is understood to mean that the hair cleaning agents according to the present disclosure preferably contains less than about 0.25% by weight, more preferably less than about 0.10% by weight, and in particular no silicones and/or mineral oils, and/or of b) i. different fatty acid esters (based on the total weight of the hair cleaning agent).

The aforementioned quantities in this case apply both to freely added silicone and/or mineral oil and/or b) i. different fatty acid esters as well as silicones, and/or mineral oils and/or b) i. different fatty acid esters, which can optionally be included as a by-product in commercial products.

In a further preferred embodiment, hair cleaning agents as contemplated herein are therefore essentially free of nonionic, alkoxylated emulsifiers and/or of c) different polymeric thickening agents.

"Substantially free" is understood to mean that the hair cleaning agents according to the present disclosure preferably contain less than about 0.10% by weight, more preferably less than about 0.05% by weight, and in particular no nonionic alkoxylated emulsifiers and/or different from c) polymeric thickening agent (based on the total weight of the hair cleaning agent).

The aforementioned quantities in this case are valid for both freely added nonionic alkoxylated emulsifiers and/or c) different polymeric thickening agents and for nonionic, alkoxylated emulsifiers and/or of c) different polymeric thickening agents, which can optionally be present as a by-product in commercial products.

In addition to the aforementioned essential and optional constituents, the hair cleaning agents as contemplated herein can contain, in a further preferred embodiment, for further increasing the care properties of the agents, at least one further hair conditioning active substance which can be selected from the group of
  protein hydrolyzates and/or
  vitamins.

Suitable protein hydrolyzates are understood to mean product mixtures which can be obtained by acid, alkaline or enzymatically catalyzed degradation of proteins.

Protein hydrolyzates of plant, animal and/or marine origin can be used.

Animal protein hydrolyzates are, for example, elastin, collagen, keratin, silk and milk protein protein hydrolyzates, which can also be present in the form of salts. Such products are sold, for example, under the trademark Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex) and Kerasol® (Croda).

Preference is given to protein hydrolyzates of plant origin, for example, soybean, almond, rice, pea, potato and wheat protein hydrolyzates. Such products are, for example, available under the trade name Gluadin® (Cognis), DiaMin® (Diamalt), Lexein® (Inolex) and Crotein® (Croda).

It is also possible to use cationized protein hydrolyzates, wherein the underlying protein hydrolyzate can originate from animal, for example, from collagen, milk or keratin, from plants, for example from wheat, corn, rice, potatoes, soy or almonds, from marine life forms, for example, from fish collages or algae, or from biotechnologically derived protein hydrolyzates. The protein hydrolyzates on which the cationic derivatives are based can be obtained from the corresponding proteins by chemical, in particular alkaline or acid hydrolysis, by enzymatic hydrolysis and/or a combination of both types of hydrolysis. The hydrolysis of proteins usually results in a protein hydrolyzate having a molecular weight distribution of about 100 daltons up to several thousand daltons. Preference is given to those cationic protein hydrolyzates whose underlying protein content has a molecular weight of from about 100 to about 25,000 daltons, preferably from about 250 to about 5000 daltons. Furthermore, cationic protein hydrolyzates are to be understood to mean quaternized amino acids and mixtures thereof. The quaternization of the protein hydrolyzates or amino acids is often carried out using quaternary ammonium salts such as N,N-dimethyl-N-(n-alkyl)-N-(2-hydroxy-3-chloro-n-propyl) ammonium halides. Furthermore, the cationic protein hydrolyzates can also be further derivatized. The products known under the INCI names and available commercially are mentioned as typical examples of the cationic protein hydrolyzates and derivatives: Cocodimonium Hydroxypropyl Hydrolyzed Collagen, Cocodimopnium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Silk, Cocodimonium Hydroxypropyl Hydrolyzed Soy Protein, Cocodimonium Hydroxypropyl Hydrolyzed Wheat Protein, Cocodimonium Hydroxypropyl Silk Amino Acids, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed keratin, Hydroxypropyltrimonium Hydrolyzed Rice Bran Protein, Hydroxyproypltrimonium Hydrolyzed Silk, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Silk, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Silk, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Silk, Quaternium-79 Hydrolyzed Soy Protein, Quaternium-79 Hydrolyzed Wheat Protein.

The proportion by weight of the protein hydrolyzate(s) in the total weight of the hair cleaning agents is preferably from about 0.01 to about 5% by weight, more preferably from about 0.025 to about 3% by weight and in particular from about 0.05 to about 2% by weight.

Suitable vitamins are preferably understood to mean the following vitamins, provitamins and vitamin precursors and their derivatives:

Vitamin A: the group of substances called vitamin A includes retinol (vitamin $A_1$) and 3,4-didehydroretinol (vitamin $A_2$). β-carotene is the provitamin of retinol. For example, vitamin A acid and its esters, vitamin A aldehyde and vitamin A alcohol and its esters such as palmitate and acetate are considered a vitamin A component.

Vitamin B: belonging to the vitamin B group or to the vitamin B complex among others Vitamin $B_1$ (thiamine)

Vitamin $B_2$ (riboflavin)

Vitamin $B_3$. The compounds nicotinic acid and nicotinamide (niacinamide) are often used under this name.

Vitamin $B_5$ (pantothenic acid and panthenol). Panthenol is preferably used in the context of this group. Useful derivatives of panthenol are in particular the esters and ethers of panthenol, pantolactone and cationically derivatized panthenols. Individual representatives are, for example, panthenol triacetate, panthenol monoethyl ether and its monoacetate, and cationic panthenol derivatives.

Vitamin $B_6$ (pyridoxine and pyridoxamine and pyridoxal).

Vitamin C (ascorbic acid): use in the form of palmitic acid ester, glucosides or phosphates can be preferred. Use in combination with tocopherols can also be preferred.

Vitamin E (tocopherols, in particular α-tocopherol).

Vitamin F: the term "vitamin F" is usually understood to mean essential fatty acids, in particular linoleic acid, linolenic acid and arachidonic acid.

Vitamin H: The compound (3aS, 4S, 6aR)-2-oxohexahydrothienol [3,4-d]imidazole-4-valeric acid is called vitamin H, for which, however, in the meantime, the trivial name biotin is used.

Particular preference is given to vitamins, provitamins and vitamin precursors from the groups A, B, E and H. Particular preference is given to nicotinamide, biotin, pantolactone and/or panthenol.

The proportion by weight of the vitamin(s), vitamin derivative(s), and/or the vitamin precursor(s) in the total weight of the hair cleaning agents is preferably from about 0.001 to about 2% by weight, particularly preferably from about 0.005 to about 1% by weight and in particular from about 0.01 to about 0.5% by weight.

It has been found that the hair cleaning agents as contemplated herein are also suitable for use as anti-dandruff preparations.

The proportion by weight of anti-dandruff agents in the total weight of the hair cleaning agent can preferably be from about 0.01 to about 10% by weight, more preferably from about 0.025 to about 7.5% by weight, particularly preferably from about 0.05 to about 5% by weight and in particular from about 0.075 to about 3% by weight.

Suitable anti-dandruff active substances can be selected from piroctone olamine, climbazole, zinc pyrithione, ketoconazole, salicylic acid, sulfur, selenium sulfide, tar preparations, undecenoic acid derivatives, burdock root extracts, poplar extracts, nettle extracts, walnut shell extracts, birch extracts, willow bark extracts, rosemary extracts and/or arnica extracts.

Preferred are climbazole, zinc pyrithione and piroctone olamine. Especially preferred is zinc pyrithione.

Further active substances, auxiliaries and additives which can preferably be present in the hair cleaning and care agents as contemplated herein are, for example:

plant extracts,
humectants,
perfumes,
UV filters,
structurants such as maleic acid,
dimethyl isosorbide,
cyclodextrins,
fiber-structure-improving active substances, in particular mono-, di- and oligosaccharides such as, for example, glucose, galactose, fructose, fruit sugar and lactose,
dyes for staining the agent,
active substances such as bisabolol and/or allantoin,
complexing agents such as EDTA, NTA, β-alanine diacetic acid and phosphonic acids,
Ceramides. Ceramides are understood to mean N-acyl-sphingosine (fatty acid amides of sphingosine) or synthetic analogues of such lipids (so-called pseudo-ceramides),
propellants such as propane-butane mixtures, $N_2O$, dimethyl ether, $CO_2$ and air,
antioxidants,
preservatives, such as sodium benzoate or salicylic acid,
additional viscosity regulators, such as salts (NaCl).

By combining the active substances a) to d) in a cosmetic carrier, preferably in water, transparent hair care shampoos can be obtained which clean the hair excellently, are well tolerated by the skin, foam very well and give the hair further improved care properties, in particular more shine, softness and volume.

As contemplated herein, particularly preferred hair cleaning agent are therefore transparent.

For the purposes of the present disclosure, "transparency" is understood to mean hair cleaning agents as contemplated herein which have an NTU value of about 50 or less, preferably of about 30 or less, wherein the determination of the NTU value is carried out at about 20° C.

In a particularly preferred embodiment, the hair cleaning agents as contemplated herein still have an NTU value of about 50 or less, preferably about 30 or less, after storage for about 12 weeks at about 40° C.

A second subject of the present disclosure is the cosmetic use of the hair cleaning agent as contemplated herein for improving the care properties of hair, in particular for improving hair shine and hair feel.

With regard to further preferred embodiments of the use as contemplated herein, what has been said about the agents as contemplated herein applies mutatis mutandis.

The following examples are intended to illustrate the subject matter of the present disclosure without, however, limiting it.

PATENT EXAMPLES a) The following hair cleaning agents as contemplated herein were produced (the amounts are based on % by weight):

|  | 1 | 2 | 3 | 4 | 5 |
|---|---|---|---|---|---|
| Anionic surfactant | 4.00-25.00 | 5.00-20.00 | 5.50-17.50 | 6.00-15.00 | 6.50-12.50 |
| Ester b) i. | 0.10-5.00 | 0.20-4.00 | 0.30-3.00 | 0.40-2.00 | 0.50-1.00 |
| Vegetable oil | 0.01-1.00 | 0.02-0.80 | 0.03-0.60 | 0.04-0.40 | 0.05-0.20 |
| Cationic guar polymer | 0.01-1.00 | 0.02-0.90 | 0.03-0.75 | 0.04-0.60 | 0.05-0.50 |
| Amidoamine of the formula (I) | 0.01-2.00 | 0.05-1.75 | 0.10-1.50 | 0.20-1.25 | 0.25-1.00 |
| Water and, if necessary, further auxiliaries and additives | ad 100 | ad 100 | ad 100 | ad 100 | ad 100 |

|  | 6 | 7 | 8 | 9 | 10 |
|---|---|---|---|---|---|
| Anionic surfactant | 4.00-25.00 | 5.00-20.00 | 5.50-17.50 | 6.00-15.00 | 6.50-12.50 |
| Glyceryl Oleate | 0.10-5.00 | 0.20-4.00 | 0.30-3.00 | 0.40-2.00 | 0.50-1.00 |
| Vegetable oil | 0.01-1.00 | 0.02-0.80 | 0.03-0.60 | 0.04-0.40 | 0.05-0.20 |
| Cationic guar polymer | 0.01-1.00 | 0.02-0.90 | 0.03-0.75 | 0.04-0.60 | 0.05-0.50 |
| Amidoamine of the formula (I) | 0.01-2.00 | 0.05-1.75 | 0.10-1.50 | 0.20-1.25 | 0.25-1.00 |
| Water and, if necessary, further auxiliaries and additives | ad 100 | ad 100 | ad 100 | ad 100 | ad 100 |

|  | 11 | 12 | 13 | 14 | 15 |
|---|---|---|---|---|---|
| Anionic surfactant | 4.00-25.00 | 5.00-20.00 | 5.50-17.50 | 6.00-15.00 | 6.50-12.50 |
| Ester b) i. | 0.10-5.00 | 0.20-4.00 | 0.30-3.00 | 0.40-2.00 | 0.50-1.00 |
| Vegetable oil | 0.01-1.00 | 0.02-0.80 | 0.03-0.60 | 0.04-0.40 | 0.05-0.20 |
| Cationic guar polymer | 0.01-1.00 | 0.02-0.90 | 0.03-0.75 | 0.04-0.60 | 0.05-0.50 |
| Brassicamidopropyl Dimethylamine | 0.01-2.00 | 0.05-1.75 | 0.10-1.50 | 0.20-1.25 | 0.25-1.00 |
| Water and, if necessary, further auxiliaries and additives | ad 100 | ad 100 | ad 100 | ad 100 | ad 100 |

-continued

|  | 16 | 17 | 18 | 19 | 20 |
|---|---|---|---|---|---|
| Anionic surfactant | 4.00-25.00 | 5.00-20.00 | 5.50-17.50 | 6.00-15.00 | 6.50-12.50 |
| Amphoteric and/or zwitterionic surfactant | 0.10-5.00 | 0.50-5.00 | 1.00-5.00 | 1.50-5.00 | 2.00-5.00 |
| Ester b) i. | 0.10-5.00 | 0.20-4.00 | 0.30-3.00 | 0.40-2.00 | 0.50-1.00 |
| Vegetable oil | 0.01-1.00 | 0.02-0.80 | 0.03-0.60 | 0.04-0.40 | 0.05-0.20 |
| Cationic guar polymer | 0.01-1.00 | 0.02-0.90 | 0.03-0.75 | 0.04-0.60 | 0.05-0.50 |
| Amidoamine of the formula (I) | 0.01-2.00 | 0.05-1.75 | 0.10-1.50 | 0.20-1.25 | 0.25-1.00 |
| Water and, if necessary, further auxiliaries and additives | ad 100 | ad 100 | ad 100 | ad 100 | ad 100 |

|  | 21 | 22 | 23 | 24 | 25 |
|---|---|---|---|---|---|
| Anionic surfactant | 4.00-25.00 | 5.00-20.00 | 5.50-17.50 | 6.00-15.00 | 6.50-12.50 |
| Amphoteric and/or zwitterionic surfactant | 0.10-5.00 | 0.50-5.00 | 1.00-5.00 | 1.50-5.00 | 2.00-5.00 |
| Nonionic surfactant | 0.05-3.00 | 0.10-2.50 | 0.20-2.25 | 0.30-2.00 | 0.40-1.50 |
| Ester b) i. | 0.10-5.00 | 0.20-4.00 | 0.30-3.00 | 0.40-2.00 | 0.50-1.00 |
| Vegetable oil | 0.01-1.00 | 0.02-0.80 | 0.03-0.60 | 0.04-0.40 | 0.05-0.20 |
| Cationic guar polymer | 0.01-1.00 | 0.02-0.90 | 0.03-0.75 | 0.04-0.60 | 0.05-0.50 |
| Amidoamine of the formula (I) | 0.01-2.00 | 0.05-1.75 | 0.10-1.50 | 0.20-1.25 | 0.25-1.00 |
| Water and, if necessary, further auxiliaries and additives | ad 100 | ad 100 | ad 100 | ad 100 | ad 100 |

|  | 26 | 27 | 28 | 29 | 30 |
|---|---|---|---|---|---|
| Anionic surfactant | 4.00-25.00 | 5.00-20.00 | 5.50-17.50 | 6.00-15.00 | 6.50-12.50 |
| Ester b) i. | 0.10-5.00 | 0.20-4.00 | 0.30-3.00 | 0.40-2.00 | 0.50-1.00 |
| Vegetable oil | 0.01-1.00 | 0.02-0.80 | 0.03-0.60 | 0.04-0.40 | 0.05-0.20 |
| Cationic guar polymer | 0.01-1.00 | 0.02-0.90 | 0.03-0.75 | 0.04-0.60 | 0.05-0.50 |
| Amidoamine of the formula (I) | 0.01-2.00 | 0.05-1.75 | 0.10-1.50 | 0.20-1.25 | 0.25-1.00 |
| Polyol | 0.50-10.00 | 0.75-9.00 | 1.00-6.00 | 1.50-5.00 | 2.00-4.00 |
| Water and, if necessary, further auxiliaries and additives | ad 100 | ad 100 | ad 100 | ad 100 | ad 100 |

|  | 31 | 32 | 33 | 34 | 35 |
|---|---|---|---|---|---|
| Anionic surfactant | 4.00-25.00 | 5.00-20.00 | 5.50-17.50 | 6.00-15.00 | 6.50-12.50 |
| Ester b) i. | 0.10-5.00 | 0.20-4.00 | 0.30-3.00 | 0.40-2.00 | 0.50-1.00 |
| Vegetable oil | 0.01-1.00 | 0.02-0.80 | 0.03-0.60 | 0.04-0.40 | 0.05-0.20 |
| Cationic guar polymer | 0.01-1.00 | 0.02-0.90 | 0.03-0.75 | 0.04-0.60 | 0.05-0.50 |
| Amidoamine of the formula (I) | 0.01-2.00 | 0.05-1.75 | 0.10-1.50 | 0.20-1.25 | 0.25-1.00 |
| Hydroxy carboxylic acid | 0.10-5.00 | 0.20-4.00 | 0.30-3.00 | 0.40-2.00 | 0.50-1.00 |
| Water and, if necessary, further auxiliaries and additives | ad 100 | ad 100 | ad 100 | ad 100 | ad 100 |

|  | 36 | 37 | 38 | 39 | 40 |
|---|---|---|---|---|---|
| Anionic surfactant | 4.00-25.00 | 5.00-20.00 | 5.50-17.50 | 6.00-15.00 | 6.50-12.50 |
| Amphoteric and/or zwitterionic surfactant | 0.10-5.00 | 0.50-5.00 | 1.00-5.00 | 1.50-5.00 | 2.00-5.00 |
| Nonionic surfactant | 0.05-3.00 | 0.10-2.50 | 0.20-2.25 | 0.30-2.00 | 0.40-1.50 |
| Ester b) i. | 0.10-5.00 | 0.20-4.00 | 0.30-3.00 | 0.40-2.00 | 0.50-1.00 |
| Vegetable oil | 0.01-1.00 | 0.02-0.80 | 0.03-0.60 | 0.04-0.40 | 0.05-0.20 |
| Cationic guar polymer | 0.01-1.00 | 0.02-0.90 | 0.03-0.75 | 0.04-0.60 | 0.05-0.50 |
| Amidoamine of the formula (I) | 0.01-2.00 | 0.05-1.75 | 0.10-1.50 | 0.20-1.25 | 0.25-1.00 |

-continued

| | | | | | |
|---|---|---|---|---|---|
| Polyol | 0.50-10.00 | 0.75-9.00 | 1.00-6.00 | 1.50-5.00 | 2.00-4.00 |
| Hydroxy carboxylic acid | 0.10-5.00 | 0.20-4.00 | 0.30-3.00 | 0.40-2.00 | 0.50-1.00 |
| Water and, if necessary, further auxiliaries and additives | ad 100 | ad 100 | ad 100 | ad 100 | ad 100 |

| | 41 | 42 | 43 | 44 | 45 |
|---|---|---|---|---|---|
| Anionic surfactant | 4.00-25.00 | 5.00-20.00 | 5.50-17.50 | 6.00-15.00 | 6.50-12.50 |
| Cocamidopropyl betaine and/or cocoampho(di)acetate | 0.10-5.00 | 0.50-5.00 | 1.00-5.00 | 1.50-5.00 | 2.00-5.00 |
| Alkyl (oligo)glycosides | 0.05-3.00 | 0.10-2.50 | 0.20-2.25 | 0.30-2.00 | 0.40-1.50 |
| Glyceryl Oleate | 0.10-5.00 | 0.20-4.00 | 0.30-3.00 | 0.40-2.00 | 0.50-1.00 |
| Vegetable oil | 0.01-1.00 | 0.02-0.80 | 0.03-0.60 | 0.04-0.40 | 0.05-0.20 |
| Guar hydroxypropyl trimonium chlorides | 0.01-1.00 | 0.02-0.90 | 0.03-0.75 | 0.04-0.60 | 0.05-0.50 |
| Brassicamidopropyl Dimethylamine | 0.01-2.00 | 0.05-1.75 | 0.10-1.50 | 0.20-1.25 | 0.25-1.00 |
| Glycerol | 0.50-10.00 | 0.75-9.00 | 1.00-6.00 | 1.50-5.00 | 2.00-4.00 |
| Lactic acid and/or citric acid | 0.10-5.00 | 0.20-4.00 | 0.30-3.00 | 0.40-2.00 | 0.50-1.00 |
| Water and, if necessary, further auxiliaries and additives | ad 100 | ad 100 | ad 100 | ad 100 | ad 100 | b) Assessment hair cleaning agent according to and not as contemplated herein

TABLE

| | 46 | 47 | 48 |
|---|---|---|---|
| Sodium Laureth Sulfate | 9.5 | 9.0 | 9.5 |
| Cocamidopropyl betaine | 3.5 | 3.0 | 3.5 |
| Disodium cocoamphodiacetate | 0.9 | | 0.9 |
| Plantacare ®[1] 818 | | 6.0 | |
| Sodium benzoate | 0.5 | 0.2 | 0.5 |
| Citric acid | 0.6 | 1 | 0.6 |
| Lactic acid | 0.12 | | |
| Sodium chloride | 0.8 | | 0.8 |
| Carbomer | | 2.5 | |
| Guar hydroxypropyltrimonium chloride (Jaguar ®[2] C 162) | 0.15 | | |
| Polyquaternium-10 | | | 0.15 |
| Polyquaternium-77 | | 0.5 | |
| Cosmedia Guar ®[3] C 261 | | 0.4 | |
| Dow Corning ®[4] 949 | | 0.5 | |
| Brassicamidopropyl Dimethylamine | 0.5 | 1.0 | |
| Steraryldimonium hydroxypropyl lauryl glucosides | | 0.5 | |
| (Bis-(ethyl isostearylimidazoline) isostearamide | | 4.0 | |
| Glutamic acid | | 0.5 | |
| Aspartic acid | | 1.0 | |
| Panthenol | | 0.5 | |
| Cetiol ®[5] C5 | | 0.3 | |
| Dicaprylyl carbonate | | 0.3 | |
| PEG-7 Glyceryl Cocoate | | | 0.5 |
| PEG-40 Hydrogenated Castor Oil | | | 0.5 |
| Coco Glucoside | 0.7 | | |
| Glyceryl Oleate | 0.6 | | 0.5 |
| Macadamia nut oil | 0.05 | | 0.05 |
| Perfume | 0.3 | 0.3 | 0.3 |
| Glycerol | 3.0 | | |
| Phenoxyethanol | | 0.4 | |
| Water | ad 100 | ad 100 | ad 100 |
| pH value | 4.5-5.8 | 4.5-5.8 | 4.5-5.8 |
| Viscosity [mPas]* | 5,000-10,000 | 5,000-10,000 | 5,000-10,000 |
| Satisfaction with care properties (average)** | 5.7 | 3.9 | 4.8 |
| Satisfaction with hair shine (average)** | 5.4 | 3.9 | 4.9 |

Composition 46 is as contemplated herein; Compositions 47 and 48 are comparative compositions ®1 INCI name: Coco Glucoside (about 52% AS), Aqua; BASF
®2 INCI name: Hydroxypropyl Guar Hydroxypropyltrimonium Chloride (87% AS), Aqua; Rhodia
®3 INCI name: Hydroxypropyl Guar Hydroxypropyltrimonium Chloride (93% AS), Aqua; BASF
®4 INCI name: Amodimethicone, Cetrimonium Chloride, Trideceth-12; Dow Corning
®5 INCI name: Coco Caprylate; BASF
* measured with Brookfield DV 2+; 20 rpm; Spindle 5; 20° C.
** The value given corresponds to the mean of the respective absolute rating of 20 subjects who had given grades 1 to 7 (with 1=not at all, 7=completely satisfied) in answering the questions: "How satisfied are you with the care properties of the product?" and "How satisfied are you with the gloss characteristics of the product?" after the application of the respective products for two weeks each. The products were packed neutral before the test and coded accordingly.

It can be seen from the results in Table 1 that the compositions as contemplated herein effect better care properties on the hair than compositions from the prior art:

Composition 47 comprises, instead of a cationic guar polymer, polyquatemium-10 and ethoxylated emulsifiers as stabilizing agent for the oil;

Composition 48 comprises a variety of cationic care substances and oils, and an thickening polymer based on acrylic acid.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A hair cleaning agent comprising:
a) at least one anionic surfactant,
b) a mixture of oils comprising
   i) at least one mono- and/or diester of glycerol and a saturated or unsaturated, branched or unbranched carboxylic acid having 18 to 30 carbon atoms, and
   ii) at least one oil selected from the group of amaranth seed oil, apricot kernel oil, argan oil, avocado oil, babassu oil, cottonseed oil, borage seed oil, camelina oil, canola oil, cranberry oil, thistle oil, peanut oil, pomegranate kernel oil, grapefruit seed oil, hemp oil, rose hip kernel oil, hazelnut oil, elderflower seed oil, currant seed oil, jojoba oil, cocoa butter, coconut oil, pumpkin seed oil, linseed oil, macadamia nut oil, maize germ oil, mallow oil, almond oil, mango seed oil, marula oil, poppy seed oil, evening primrose oil, olive oil, palm oil, palm kernel oil, peach kernel oil, rambutan oil, rapeseed oil, rice bran oil, castor oil, sacha inchi oil, safflower oil, sea buckthorn pulp oil, sea buckthorn seed oil, sasanqua oil, sesame oil, shea butter, soybean oil, sunflower oil, tea tree oil, grapeseed oil, tsubaki oil, walnut oil, wheat germ oil, meadowfoam seed oil, wild rose oil, and combinations thereof, wherein the total amount of ii) present in the agent is in an amount of from 0.01 to 1.00% by weight based on the total weight of the agent,
c) at least one cationic guar polymer, and
d) at least one amidoamine of the formula (I)

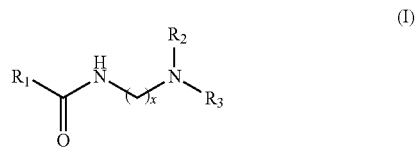

wherein
$R_1$ stands for a saturated or unsaturated, branched or unbranched alk(en)yl radical having 19 to 30 carbon atoms,
$R_2$ and $R_3$ independently stand for hydrogen or a $C_1$-$C_4$ alkyl group, and x stands for an integer from 2 to 6.

2. The hair cleaning agent according to claim 1, comprising, based on the total weight of the agent,
from about 4.00 to about 25.00% by weight of the at least one anionic surfactant a),
from about 0.10 to about 5.00% by weight of the at least one mono- and/or diester b i),
from 0.02 to 0.80% by weight of the at least one oil b ii),
from about 0.01 to about 1.00% by weight of the at least one cationic guar polymer c),
from about 0.01 to about 2.00% by weight of the at least one amidoamine d) according to formula (I).

3. The hair cleaning agent according to claim 1, wherein the at least one mono- and/or diester b i) is selected from mono- and/or diesters of glycerol and unsaturated carboxylic acids having 18 to 24 carbon atoms.

4. The hair cleaning agent according to claim 1, wherein the at least one mono- and/or diester b i) is selected from among the glycerol esters known under the International Nomenclature Cosmetic Ingredient (INCI) name glyceryl oleate.

5. The hair cleaning agent according to claim 1, wherein the at least one amidoamine d) is selected from compounds of the formula (I), wherein
$R_1$ stands for an alkenyl radical having 20 to 24 carbon atoms,
$R_2$ and $R_3$ stands for methyl groups, and
x stands for the numbers 2, 3 or 4.

6. The hair cleaning agent according to claim 1, wherein the at least one amidoamine d) is selected from amidoamines known under the International Nomenclature Cosmetic Ingredient (INCI) name brassicamidopropyl dimethylamine.

7. The hair cleaning agent according to claim 1, containing, based on the total weight of the agent,
from about 0.10 to about 5.00% by weight of at least one amphoteric and/or zwitterionic surfactant and/or
from about 0.05 to about 3.00% by weight of at least one nonionic surfactant.

8. The hair cleaning agent according to claim 1, containing, based on the total weight of the agent, from about 0.50 to about 10.00% by weight of at least one polyol.

9. The hair cleaning agent according to claim 8, wherein the polyol is glycerol in a weight proportion of from about 1.00 to about 6.00% by weight of the total weight of the hair cleaning agent.

10. The hair cleaning agent according to claim 1, containing, based on the total weight of the agent, from about 0.10 to about 5.00% by weight of at least one hydroxycarboxylic acid.

11. The hair cleaning agent according to claim 1, wherein the hair cleaning agent is substantially free of nonionic, alkoxylated emulsifiers and/or of c) different polymeric thickening agents.

12. The hair cleaning agent according to claim 1, wherein the hair cleaning agent is substantially free of silicones and/or mineral oils and/or of b i) different fatty acid esters.

13. The hair cleaning agent according to claim 1, wherein the hair cleaning agent is transparent.

14. The hair cleaning agent according to claim 1, wherein the hair cleaning agent further comprises, based on the total weight of the agent, at least about 75% by weight of water.

15. A method for improving the care properties of hair, the method comprising applying a hair cleaning agent to the hair, the hair cleaning agent comprising:
   a) at least one anionic surfactant,
   b) a mixture of oils comprising
      i) at least one mono- and/or diester of glycerol and a saturated or unsaturated, branched or unbranched carboxylic acid having 18 to 30 carbon atoms, and
      ii) at least one oil selected from the group of amaranth seed oil, apricot kernel oil, argan oil, avocado oil, babassu oil, cottonseed oil, borage seed oil, camelina oil, canola oil, cranberry oil, thistle oil, peanut oil, pomegranate kernel oil, grapefruit seed oil, hemp oil, rose hip kernel oil, hazelnut oil, elderflower seed oil, currant seed oil, jojoba oil, cocoa butter, coconut oil, pumpkin seed oil, linseed oil, macadamia nut oil, maize germ oil, mallow oil, almond oil, mango seed oil, marula oil, poppy seed oil, evening primrose oil, olive oil, palm oil, palm kernel oil, peach kernel oil, rambutan oil, rapeseed oil, rice bran oil, castor oil, sacha inchi oil, safflower oil, sea buckthorn pulp oil, sea buckthorn seed oil, sasanqua oil, sesame oil, shea butter, soybean oil, sunflower oil, tea tree oil, grapeseed oil, tsubaki oil, walnut oil, wheat germ oil, meadowfoam seed oil, wild rose oil, and combinations thereof, wherein the total amount of ii) present in the agent is in an amount of from 0.01 to 1.00% by weight based on the total weight of the agent,
   c) at least one cationic guar polymer, and
   d) at least one amidoamine of the formula (I)

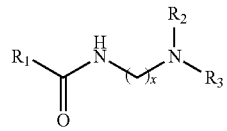

wherein
   $R_1$ stands for a saturated or unsaturated, branched or unbranched alk(en)yl radical having 19 to 30 carbon atoms,
   $R_2$ and $R_3$ independently stand for hydrogen or a $C_1$-$C_4$ alkyl group, and x stands for an integer from 2 to 6.

* * * * *